US00PP21046P2

(12) United States Plant Patent
Klemm et al.

(10) Patent No.: US PP21,046 P2
(45) Date of Patent: Jun. 1, 2010

(54) ***CALIBRACHOA* PLANT NAMED 'KLECA08167'**

(50) Latin Name: ***Calibrachoa* hybrid**
Varietal Denomination: KLECA08167

(75) Inventors: Nils Klemm, Stuttgart (DE); Anita Stoever, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/383,927

(22) Filed: Mar. 30, 2009

(51) Int. Cl.
*A01H 5/00* (2006.01)

(52) U.S. Cl. ..... Plt./413

(58) Field of Classification Search ..... Plt./413
See application file for complete search history.

*Primary Examiner*—Kent L Bell
(74) *Attorney, Agent, or Firm*—Jondle & Associates, P.C.

(57) ABSTRACT

A new *Calibrachoa* plant named 'KLECA08167' particularly distinguished by light yellow flowers, very good branching habit, and a vigorous and semi-trailing growth habit, is disclosed.

1 Drawing Sheet

*Calibrachoa* Plant Named 'KLECA08167'

Genus and species

*Calibrachoa* hybrid

Variety denomination

'KLECA08167'

BACKGROUND OF THE NEW PLANT

The present invention comprises a new and distinct cultivar of *Calibrachoa,* botanically known as *Calibrachoa* hybrid and hereinafter referred to by the cultivar name 'KLECA08167'. The new cultivar originated from a self-pollination made in Summer 2004 in Stuttgart, Germany from the proprietary *Calibrachoa* parent plant 'V 182' (unpatented).

The new cultivar was first propagated in May 2005 by vegetative cuttings in Stuttgart, Germany and has been asexually reproduced by vegetative cuttings in Stuttgart, Germany for more than 30 generations. The present invention has been found to retain its distinctive characteristics through successive asexual propagations.

Plant Breeder's Rights for this cultivar have been applied for in Canada on Jan. 31, 2008. 'KLECA08167' has not been made publicly available more than one year prior to the filing date of this application.

SUMMARY OF THE INVENTION

The following are the most outstanding and distinguishing characteristics of this new cultivar when grown under normal horticultural practices in Stuttgart, Germany.

1. Light yellow flowers;
2. Very good branching habit; and
3. A vigorous and semi-trailing growth habit.

DESCRIPTION OF THE PHOTOGRAPH

This new *Calibrachoa* plant is illustrated by the accompanying photograph which shows flowers and foliage of the plant; the colors shown are as true as can be reasonably obtained by conventional photographic procedures. The photograph is of a five-month-old *Calibrachoa* plant, grown in a greenhouse in Stuttgart, Germany, between January and May 2008.

DESCRIPTION OF THE NEW CULTIVAR

The following detailed descriptions set forth the distinctive characteristics of 'KLECA08167'. The data which defines these characteristics were collected from asexual reproductions carried out in Stuttgart, Germany. The plant history was taken on five-month-old plants which were planted as rooted cuttings in 11-cm pots between January and May 2008 and then grown in a greenhouse. The plants had one terminal pinch one week after potting. Color readings were taken under natural light. Color references are primarily to the RHS Colour Chart of The Royal Horticultural Society of London (RHS) (2001).

DETAILED BOTANICAL DESCRIPTION OF THE NEW PLANT

Classification:
- *Family.*—Solanaceae.
- *Botanical.*—*Calibrachoa* hybrid.
- *Common.*—*Calibrachoa.*

Parentage: The new cultivar originated from a self-pollination from the proprietary *Calibrachoa* parent plant 'V 182' (unpatented).

Growth:
- *Habit.*—Vigorous and semi-trailing.
- *Height* (*measured from the top of the soil*).—13.0 cm.
- *Width* (*horizontal plant diameter*).—20.0 cm.
- *Time to produce a finished flowering plant.*—8 weeks.
- *Outdoor plant performance.*—Continuous flowering.
- *Time to initiate and develop roots.*—16 days.
- *Root description.*—Moderate density, freely branching with white roots.

Stems:
- *Length of basal branches.*—10.0 cm.
- *Internode length.*—0.8 cm to 1.5 cm.

*Diameter of branches* (*from midpoint*).—0.2 cm to 0.6 cm.
*Stem color.*—RHS 144A.
*Texture.*—Smooth.
*Anthocyanin.*—Absent.
*Pedicel.*—Color: RHS 144A. Length: 1.8 cm. Diameter: 0.2 cm. Texture: Smooth.

Leaves:
*Arrangement.*—Alternate.
*Size.*—Length: 0.7 cm to 3.0 cm. Width: 0.2 cm to 0.9 cm.
*Shape.*—Lanceolate to broad elliptic.
*Apex.*—Broadly acute.
*Base.*—Attenuate.
*Margin.*—Entire.
*Color.*—Immature and mature: Upper surface: RHS 137B. Lower surface: RHS 137C.
*Texture* (*both surfaces*).—Smooth.
*Venation.*—Pinnate.
*Venation color.*—RHS 145A.
*Petioles.*—Absent.

Flower bud:
*Shape.*—Irregular to oblong.
*Size.*—Length: 1.9 cm. Diameter: 0.6 cm.
*Color at tight bud.*—RHS 154C.

Inflorescence:
*Blooming habit.*—Continuous flowering during summertime.
*Inflorescence type.*—Single.
*Floret type.*—Funnel-shaped.
*Lastingness of individual blooms on the plant.*—6 days.
*Fragrance.*—Absent.

Flowers:
*Immature flower.*—Diameter: Horizontal: 2.8 cm. Vertical: 2.4 cm. Color: Upper surface: RHS 3A. Lower surface: RHS 3C.
*Mature flower.*—Diameter: Horizontal: 3.0 cm. Vertical: 2.6 cm. Color: Upper surface: RHS 3A. Lower surface: RHS 3C.
*Corolla tube.*—Color inside: RHS 7A. Color outside: RHS 3C. Tube length: 1.7 cm. Outside texture: Smooth. Inside texture: Smooth.
*Petals.*—Apex: Obverse. Base: Fused into the tube. Margin: Entire. Waviness of petals: Weak. Lobation: Weak. Texture (both surfaces): Smooth.
*Sepals.*—Calyx (form): Rosette. Shape: Lanceolate to elliptic. Apex: Acute. Base: Base fused into the tube. Margin: Entire. Length: 1.3 cm. Width: 0.3 cm. Color: Upper surface: RHS 138A. Lower surface: RHS 138B. Texture (both surfaces): Smooth.

Reproductive organs:
*Stamens.*—Number: 5. Filament color: RHS 2C. Filament length: 0.7 cm and 1.0 cm. Filament diameter: 0.1 cm. Pollen color: RHS 7A. Pollen quantity: Sparse.
*Pistils.*—Number: 1. Length: 0.6 cm. Diameter: 0.1 cm. Stigma color: RHS 149B. Style color: RHS 149A.

Fruit and Seed Set: No seed set observed.

Disease and insect resistance: No particular resistance or susceptibility has been observed but sometimes aphid sensitivity is observed.

COMPARISON WITH PARENTAL AND COMMERCIAL CULTIVARS

'KLECA08167' differs from the self-pollination parent 'V 182' (unpatented) in that 'KLECA08167' has light yellow flowers and a vigorous and semi-trailing growth habit, while 'V 182' has apricot-colored flowers and a vigorous and trailing growth habit.

'KLECA08167' differs from the commercial cultivar 'KLECA06098' (U.S. Plant patent applicaton No. 12/002,478, Abandoned) in that 'KLECA08167' has light yellow flowers and a vigorous and semi-trailing growth habit, while 'KLECA06098' has yellow flowers and a compact and mounding growth habit.

I claim:

1. A new and distinct cultivar of *Calibrachoa* plant named 'KLECA08167' as shown and described herein.

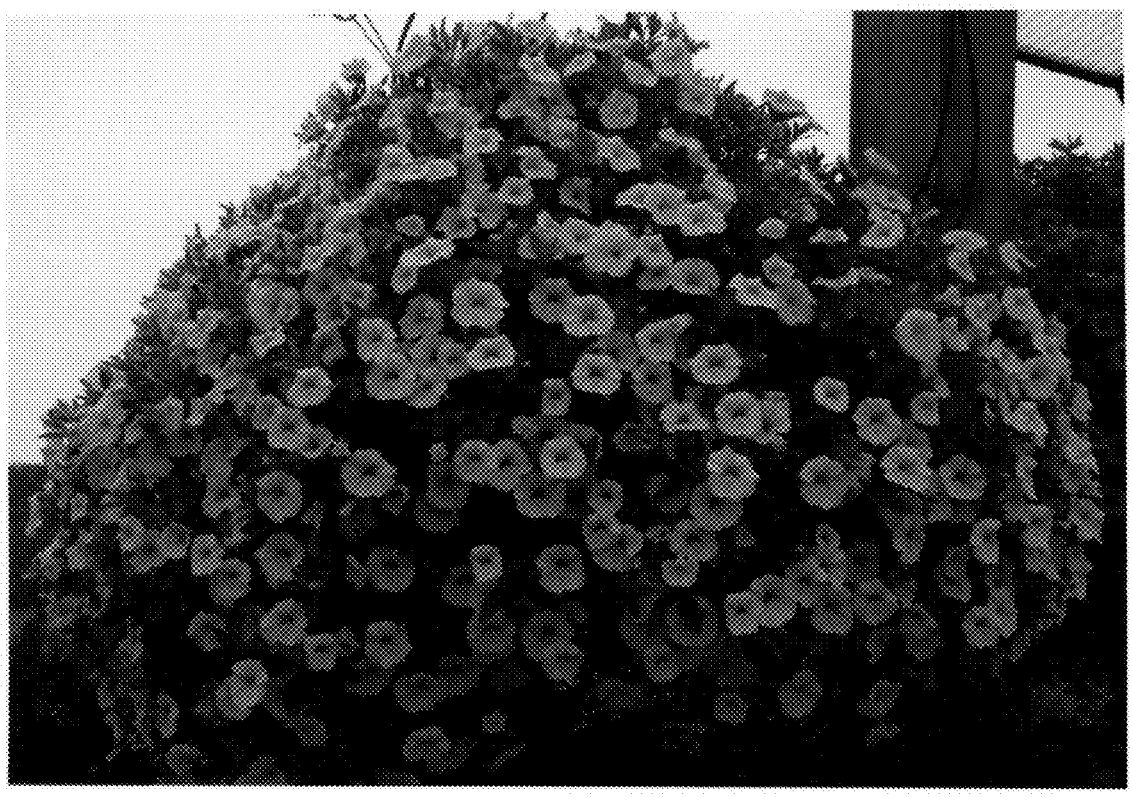

* * * * *